US012636167B2

(12) United States Patent　　　　(10) Patent No.:　US 12,636,167 B2
Clemens et al.　　　　　　　　　　(45) Date of Patent:　　　May 26, 2026

(54) INTERBODY DEVICE INCORPORATING LATTICE STRUCTURE AND RELATED SYSTEMS AND METHODS

(71) Applicant: Mighty Oak Medical, Inc., Englewood, CO (US)

(72) Inventors: Austin Clemens, Denver, CO (US); Tyler Drumm, Littleton, CO (US); Caleb Voelkel, Lakewood, CO (US); George Frey, Englewood, CO (US)

(73) Assignee: Mighty Oak Medical, Inc., Englewood, CO (US)

( * ) Notice: Subject to any disclaimer, the term of this patent is extended or adjusted under 35 U.S.C. 154(b) by 94 days.

(21) Appl. No.: 18/583,767

(22) Filed: Feb. 21, 2024

(65) Prior Publication Data

US 2024/0277487 A1　　　Aug. 22, 2024

Related U.S. Application Data

(60) Provisional application No. 63/447,299, filed on Feb. 21, 2023.

(51) Int. Cl.
*A61F 2/44*　　　(2006.01)
*A61F 2/30*　　　(2006.01)

(52) U.S. Cl.
CPC .......... *A61F 2/447* (2013.01); *A61F 2/30771* (2013.01); *A61F 2/30942* (2013.01);
(Continued)

(58) Field of Classification Search
CPC .... A61F 2/30771; A61F 2/447; A61F 2/4455; A61F 2/30942; A61F 2002/2835; A61F 2002/30011
See application file for complete search history.

(56) References Cited

U.S. PATENT DOCUMENTS 755,994 A　　3/1904　Broome
3,151,392 A　10/1964　Chambers
(Continued)

FOREIGN PATENT DOCUMENTS

CA　　　2736525　　　3/2010
CA　　　2862341　　　8/2013
(Continued)

OTHER PUBLICATIONS

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
(Continued)

*Primary Examiner* — Eduardo C Robert
*Assistant Examiner* — Holly Joanna Lane
(74) *Attorney, Agent, or Firm* — FisherBroyles LLP; Ian R. Walsworth

(57)　　　　　ABSTRACT

The present disclosure includes an orthopedic device, such as an implant, that comprises one or more latticed regions to aid in fusion or osteo-integration between the implant and a specific patient. The implant may have periodic, organic, hybrid lattice structures or a combination thereof to further facilitate biocompatibility and improve mechanical characteristics of the implant. Methods for fabricating a customized device are also described herein.

19 Claims, 4 Drawing Sheets

(52) U.S. Cl.
    CPC .............. *A61F 2002/30011* (2013.01); *A61F 2002/30153* (2013.01); *A61F 2002/30158* (2013.01); *A61F 2002/30304* (2013.01); *A61F 2002/30324* (2013.01); *A61F 2002/30383* (2013.01); *A61F 2002/30827* (2013.01); *A61F 2002/3092* (2013.01)

(56)                References Cited

U.S. PATENT DOCUMENTS

| | | | |
|---|---|---|---|
| 5,092,866 A | 3/1992 | Breard |
| 5,129,904 A | 7/1992 | Illi |
| 5,201,734 A | 4/1993 | Cozad et al. |
| 5,291,901 A | 3/1994 | Graf |
| 5,334,204 A | 8/1994 | Clewett et al. |
| 5,360,448 A | 11/1994 | Thramann |
| 5,387,213 A | 2/1995 | Breard et al. |
| D359,557 S | 6/1995 | Hayes |
| 5,490,409 A | 2/1996 | Weber |
| 5,527,312 A | 6/1996 | Ray |
| 5,562,737 A | 10/1996 | Graf |
| 5,569,246 A | 10/1996 | Ojima et al. |
| 5,591,233 A | 1/1997 | Kelman et al. |
| 5,725,581 A | 3/1998 | Brånemark |
| D403,066 S | 12/1998 | DeFonzo |
| 5,865,846 A | 2/1999 | Bryan et al. |
| RE36,221 E | 6/1999 | Breard |
| D412,032 S | 7/1999 | Mikula-Curtis et al. |
| 5,961,516 A | 10/1999 | Graf |
| 5,993,453 A | 11/1999 | Bullara et al. |
| 6,006,581 A | 12/1999 | Holmes |
| D420,132 S | 2/2000 | Bucholz et al. |
| 6,030,401 A | 2/2000 | Marino |
| 6,035,691 A | 3/2000 | Lin et al. |
| 6,048,343 A | 4/2000 | Mathis |
| 6,063,088 A | 5/2000 | Winslow |
| D428,989 S | 8/2000 | Segermark et al. |
| 6,113,602 A | 9/2000 | Sand |
| 6,142,998 A | 11/2000 | Smith et al. |
| 6,221,077 B1 | 4/2001 | Rinner et al. |
| 6,290,724 B1 | 9/2001 | Marino |
| 6,309,395 B1 | 10/2001 | Smith et al. |
| 6,328,738 B1 | 12/2001 | Suddaby |
| 6,364,880 B1 | 4/2002 | Michelson |
| 6,402,750 B1 | 6/2002 | Atkinson et al. |
| 6,445,211 B1 | 9/2002 | Saripella |
| 6,565,572 B2 | 5/2003 | Chappius |
| 6,644,087 B1 | 11/2003 | Ralph et al. |
| 6,663,633 B1 | 12/2003 | Pierson |
| 6,711,432 B1 | 3/2004 | Krause et al. |
| 6,719,795 B1 | 4/2004 | Cornwall |
| 6,755,839 B2 | 6/2004 | Van Hoeck et al. |
| 6,835,207 B2 | 12/2004 | Zacouto |
| 6,863,671 B1 | 3/2005 | Strobel et al. |
| 7,014,640 B2 | 3/2006 | Kemppanien et al. |
| 7,025,769 B1 | 4/2006 | Ferree |
| 7,066,957 B2 | 6/2006 | Graf |
| 7,077,864 B2 | 7/2006 | Byrd, III et al. |
| D532,515 S | 11/2006 | Buttler et al. |
| D533,664 S | 12/2006 | Buttler et al. |
| 7,207,992 B2 | 4/2007 | Ritland |
| 7,235,076 B2 | 6/2007 | Pacheco |
| 7,261,716 B2 | 8/2007 | Strobel et al. |
| 7,288,093 B2 | 10/2007 | Michelson |
| 7,291,150 B2 | 11/2007 | Graf |
| 7,341,590 B2 | 3/2008 | Ferree |
| 7,387,643 B2 | 6/2008 | Michelson |
| 7,406,775 B2 | 8/2008 | Funk et al. |
| 7,454,939 B2 | 11/2008 | Garner et al. |
| 7,491,180 B2 | 2/2009 | Pacheco |
| 7,537,664 B2 | 5/2009 | O'Neill et al. |
| 7,559,931 B2 | 7/2009 | Stone |
| 7,578,851 B2 | 8/2009 | Dong et al. |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,854,752 B2 | 12/2010 | Colleran et al. |
| 7,955,355 B2 | 6/2011 | Cin |
| 7,957,824 B2 | 6/2011 | Boronvinskih et al. |
| 7,957,831 B2 | 6/2011 | Isaacs |
| 7,967,868 B2 | 6/2011 | White et al. |
| 8,057,482 B2 | 11/2011 | Stone et al. |
| 8,070,752 B2 | 12/2011 | Metzger et al. |
| 8,092,465 B2 | 1/2012 | Metzger et al. |
| 8,118,815 B2 | 2/2012 | van der Walt |
| 8,159,753 B2 | 4/2012 | Ojeda et al. |
| 8,167,884 B2 | 5/2012 | Pacheco |
| 8,175,683 B2 | 5/2012 | Roose |
| 8,206,396 B2 | 6/2012 | Trabish |
| 8,214,014 B2 | 7/2012 | Pacheco |
| 8,236,006 B2 | 8/2012 | Hamada |
| 8,241,293 B2 | 8/2012 | Stone |
| 8,257,083 B2 | 9/2012 | Berckmans et al. |
| D669,176 S | 10/2012 | Frey |
| D669,984 S | 10/2012 | Cheney et al. |
| 8,277,461 B2 | 10/2012 | Pacheco |
| 8,282,646 B2 | 10/2012 | Schoenefeld |
| 8,298,235 B2 | 10/2012 | Grinberg |
| 8,298,237 B2 | 10/2012 | Schoenefeld |
| 8,298,242 B2 | 10/2012 | Justis et al. |
| D672,038 S | 12/2012 | Frey |
| 8,323,322 B2 | 12/2012 | Dawson et al. |
| 8,357,111 B2 | 1/2013 | Caillouette et al. |
| 8,377,066 B2 | 2/2013 | Katrana et al. |
| 8,407,067 B2 | 3/2013 | Ulthgenannt et al. |
| 8,419,740 B2 | 4/2013 | Aram et al. |
| D685,087 S | 6/2013 | Voic |
| 8,460,303 B2 | 6/2013 | Park |
| 8,475,505 B2 | 7/2013 | Nebosky et al. |
| 8,480,679 B2 | 7/2013 | Park et al. |
| 8,535,387 B2 | 9/2013 | Meridew et al. |
| 8,540,719 B2 | 9/2013 | Peukert et al. |
| 8,545,509 B2 | 10/2013 | Park et al. |
| 8,549,888 B2 | 10/2013 | Isaacs |
| 8,568,487 B2 | 10/2013 | Witt et al. |
| 8,591,516 B2 | 11/2013 | Metzger et al. |
| 8,603,180 B2 | 12/2013 | White et al. |
| 8,607,603 B2 | 12/2013 | Justis et al. |
| 8,608,748 B2 | 12/2013 | Metzger et al. |
| 8,608,749 B2 | 12/2013 | Witt et al. |
| 8,632,547 B2 | 1/2014 | Metzger et al. |
| 8,668,700 B2 | 3/2014 | Catanzarite |
| 8,671,572 B2 | 3/2014 | Schlottig et al. |
| D705,929 S | 5/2014 | Frey |
| 8,721,651 B2 | 5/2014 | Loke et al. |
| 8,758,357 B2 | 6/2014 | Frey et al. |
| 8,808,302 B2 | 8/2014 | White et al. |
| 8,808,303 B2 | 8/2014 | Stemniski et al. |
| 8,821,506 B2 | 9/2014 | Mitchell |
| 8,858,561 B2 | 10/2014 | White et al. |
| 8,864,769 B2 | 10/2014 | Stone et al. |
| 8,870,889 B2 | 10/2014 | Frey et al. |
| D718,862 S | 12/2014 | Matheny |
| D718,863 S | 12/2014 | Matheny |
| D718,864 S | 12/2014 | Matheny |
| 8,900,279 B2 | 12/2014 | Assell et al. |
| 8,979,749 B2 | 3/2015 | Gorek et al. |
| 8,979,911 B2 | 3/2015 | Martineau et al. |
| 8,992,538 B2 | 3/2015 | Keefer |
| D726,914 S | 4/2015 | Matheny |
| 9,017,412 B2 | 4/2015 | Wolters et al. |
| 9,044,285 B2 | 6/2015 | Harper |
| 9,066,727 B2 | 6/2015 | Catanzarite et al. |
| 9,066,816 B2 | 6/2015 | Allard et al. |
| 9,113,971 B2 | 8/2015 | Metzger et al. |
| D738,498 S | 9/2015 | Frey et al. |
| 9,138,325 B2 | 9/2015 | Mouw |
| 9,173,661 B2 | 11/2015 | Metzger et al. |
| 9,173,692 B1 | 11/2015 | Unm |
| D745,671 S | 12/2015 | Frey et al. |
| D745,672 S | 12/2015 | Frey et al. |
| D745,673 S | 12/2015 | Frey et al. |
| 9,198,678 B2 | 12/2015 | Frey et al. |

(56) References Cited

U.S. PATENT DOCUMENTS

| | | |
|---|---|---|
| 9,198,702 B2 | 12/2015 | Biedermann et al. |
| 9,289,253 B2 | 3/2016 | Sweeney |
| 9,451,973 B2 | 9/2016 | Heilman et al. |
| 9,456,901 B2 | 10/2016 | Jones et al. |
| 9,486,324 B2 | 11/2016 | Hochschuler |
| D775,335 S | 12/2016 | Frey et al. |
| 9,642,633 B2 | 5/2017 | Frey et al. |
| 9,649,160 B2 | 5/2017 | van der Walt et al. |
| 9,662,157 B2 | 5/2017 | Schneider et al. |
| 9,675,400 B2 | 6/2017 | Katrana et al. |
| 9,737,339 B2 | 8/2017 | Copp et al. |
| 9,814,497 B1 | 11/2017 | Al-Habib et al. |
| 9,826,991 B2 | 11/2017 | Kaiser et al. |
| 9,839,448 B2 | 12/2017 | Reckling et al. |
| 9,848,922 B2 | 12/2017 | Tohmeh et al. |
| 9,913,669 B1 | 3/2018 | Scholl et al. |
| 9,949,843 B2 | 4/2018 | Reiley et al. |
| 9,968,408 B1 | 5/2018 | Casey et al. |
| 9,987,024 B2 | 6/2018 | Frey et al. |
| 10,085,784 B2 | 10/2018 | Ono et al. |
| 10,166,033 B2 | 1/2019 | Keiley et al. |
| 10,369,009 B2* | 8/2019 | Joly ..................... A61F 2/4465 |
| 11,376,049 B2 | 7/2022 | Frey et al. |
| 11,376,073 B2 | 7/2022 | Frey et al. |
| 11,633,254 B2 | 4/2023 | Frey et al. |
| 12,251,318 B2* | 3/2025 | Rucker .................. B33Y 80/00 |
| 2004/0097925 A1 | 5/2004 | Boehm et al. |
| 2004/0144149 A1 | 7/2004 | Strippgen et al. |
| 2004/0147929 A1 | 7/2004 | Biedermann et al. |
| 2004/0225292 A1 | 11/2004 | Sasso |
| 2004/0243481 A1 | 12/2004 | Bradbury et al. |
| 2004/0267260 A1 | 12/2004 | Mack |
| 2005/0085815 A1 | 4/2005 | Harms et al. |
| 2005/0148843 A1 | 7/2005 | Roose |
| 2005/0177156 A1 | 8/2005 | Timm et al. |
| 2005/0203514 A1 | 9/2005 | Tae-Ahn |
| 2005/0203519 A1 | 9/2005 | Jurgen |
| 2005/0262911 A1 | 12/2005 | Dankowicz et al. |
| 2005/0288672 A1 | 12/2005 | Ferree |
| 2006/0036323 A1 | 2/2006 | Carl |
| 2006/0058792 A1 | 3/2006 | Hynes |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2006/0247642 A1 | 11/2006 | Stone |
| 2006/0264935 A1 | 11/2006 | White |
| 2007/0088359 A1 | 4/2007 | Woods |
| 2007/0093813 A1 | 4/2007 | Callahan |
| 2007/0093832 A1 | 4/2007 | Abdelgany |
| 2007/0100341 A1 | 5/2007 | Reglos |
| 2007/0161985 A1 | 7/2007 | Demakas et al. |
| 2007/0198014 A1 | 8/2007 | Graf et al. |
| 2007/0227216 A1 | 10/2007 | Schalliol |
| 2007/0233123 A1 | 10/2007 | Ahmad et al. |
| 2007/0270858 A1 | 11/2007 | Trieu et al. |
| 2007/0288011 A1 | 12/2007 | Logan |
| 2007/0288030 A1 | 12/2007 | Metzger et al. |
| 2008/0039846 A1 | 2/2008 | Lee |
| 2008/0086127 A1 | 4/2008 | Patterson et al. |
| 2008/0114370 A1 | 5/2008 | Schoenefeld |
| 2008/0161815 A1 | 7/2008 | Schoenefeld et al. |
| 2008/0183214 A1 | 7/2008 | Copp et al. |
| 2008/0255564 A1 | 10/2008 | Michelson |
| 2008/0257363 A1 | 10/2008 | Schoenefeld et al. |
| 2008/0275452 A1 | 11/2008 | Lang et al. |
| 2008/0306552 A1 | 12/2008 | Winslow |
| 2008/0312659 A1 | 12/2008 | Metzger et al. |
| 2008/0319491 A1 | 12/2008 | Schoenefeld |
| 2009/0076555 A1 | 3/2009 | Lowry et al. |
| 2009/0087276 A1 | 4/2009 | Rose |
| 2009/0088674 A1 | 4/2009 | Caillouette et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0105760 A1 | 4/2009 | Frey |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2009/0318981 A1 | 12/2009 | Kang |
| 2009/0326537 A1 | 12/2009 | Anderson |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100135 A1 | 4/2010 | Phan |
| 2010/0100193 A1 | 4/2010 | White |
| 2010/0106199 A1 | 4/2010 | Sawa |
| 2010/0152782 A1 | 6/2010 | Stone et al. |
| 2010/0185204 A1 | 7/2010 | Buttermann et al. |
| 2010/0191244 A1 | 7/2010 | White et al. |
| 2010/0217270 A1 | 8/2010 | Polinski et al. |
| 2010/0217336 A1 | 8/2010 | Crawford et al. |
| 2010/0298889 A1 | 11/2010 | Lothar |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046628 A1 | 2/2011 | Jamali |
| 2011/0046735 A1 | 2/2011 | Metzger et al. |
| 2011/0054478 A1 | 3/2011 | Vanasse et al. |
| 2011/0060373 A1 | 3/2011 | Russell |
| 2011/0071533 A1 | 3/2011 | Metzger et al. |
| 2011/0093023 A1 | 4/2011 | Lee et al. |
| 2011/0093086 A1 | 4/2011 | Witt et al. |
| 2011/0112436 A1 | 5/2011 | Jones et al. |
| 2011/0137352 A1 | 6/2011 | Lutz |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2011/0319745 A1 | 12/2011 | Frey |
| 2012/0041445 A1 | 2/2012 | Roose et al. |
| 2012/0130434 A1 | 5/2012 | Stemniski et al. |
| 2012/0150243 A9 | 6/2012 | Crawford et al. |
| 2012/0179259 A1 | 7/2012 | McDonough et al. |
| 2012/0215315 A1 | 8/2012 | Hochschuler et al. |
| 2012/0245587 A1 | 9/2012 | Fang |
| 2013/0006251 A1 | 1/2013 | Aram et al. |
| 2013/0053854 A1 | 2/2013 | Schoenefeld et al. |
| 2013/0110174 A1 | 5/2013 | Marik |
| 2013/0123850 A1 | 5/2013 | Schoenefeld et al. |
| 2013/0218163 A1 | 8/2013 | Frey |
| 2014/0137618 A1 | 5/2014 | Isaacs |
| 2014/0350614 A1 | 11/2014 | Frey |
| 2014/0379032 A1 | 12/2014 | Hennard |
| 2015/0018956 A1* | 1/2015 | Steinmann ................ A61F 2/34 |
| | | 419/53 |
| 2015/0047410 A1 | 2/2015 | Petit et al. |
| 2015/0127053 A1 | 5/2015 | Maruenda Paulino et al. |
| 2015/0297249 A1 | 10/2015 | Catanzarite |
| 2016/0030067 A1 | 2/2016 | Frey et al. |
| 2016/0166301 A1 | 6/2016 | Papangelou et al. |
| 2016/0270802 A1 | 9/2016 | Fang et al. |
| 2017/0215857 A1 | 8/2017 | D'Urso |
| 2017/0252107 A1* | 9/2017 | Turner ..................... G06N 5/04 |
| 2017/0312032 A1 | 11/2017 | Amanatullah et al. |
| 2018/0042646 A1 | 2/2018 | Frey et al. |
| 2018/0082480 A1 | 3/2018 | White |
| 2018/0168740 A1 | 6/2018 | Ryan et al. |
| 2018/0256336 A1* | 9/2018 | Mueller ................ A61F 2/2846 |
| 2018/0317971 A1 | 11/2018 | Prevost |
| 2019/0076266 A1* | 3/2019 | Trudeau .............. A61F 2/30965 |
| 2019/0117410 A1* | 4/2019 | Parry ................... A61F 2/0077 |

(56)                    References Cited

U.S. PATENT DOCUMENTS

| | | | |
|---|---|---|---|
| 2019/0167326 A1 | 6/2019 | Greenhalgh et al. | |
| 2019/0343566 A1 | 11/2019 | Tempco et al. | |
| 2019/0343567 A1 | 11/2019 | Tempco et al. | |
| 2022/0117753 A1* | 4/2022 | Rucker | B33Y 10/00 |
| 2024/0115398 A1* | 4/2024 | Frey | A61F 2/4425 |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 2002531214 | 9/2002 |
| JP | 2006-528533 | 12/2006 |
| JP | 2007510482 | 4/2007 |
| JP | 2008-514362 | 5/2008 |
| JP | 2012-143379 | 8/2012 |
| JP | D1508406 | 10/2014 |
| WO | WO2001037728 | 8/2002 |
| WO | WO2004071314 | 8/2004 |
| WO | WO2005003710 | 1/2005 |
| WO | WO2006039266 | 4/2006 |
| WO | WO2006066053 | 6/2006 |
| WO | WO2006079531 | 8/2006 |
| WO | WO2007037920 | 4/2007 |
| WO | WO2007145937 | 12/2007 |
| WO | WO2008027549 | 3/2008 |
| WO | WO2009004625 | 1/2009 |
| WO | WO2009035358 | 3/2009 |
| WO | WO2006017641 | 4/2009 |
| WO | WO2008157412 | 4/2009 |
| WO | WO2009129063 | 10/2009 |
| WO | WO2009105106 | 12/2009 |
| WO | WO2010033431 | 3/2010 |
| WO | WO2010148103 | 12/2010 |
| WO | WO2011041398 | 4/2011 |
| WO | WO2011080260 | 7/2011 |
| WO | WO2011106711 | 9/2011 |
| WO | WO2011109260 | 9/2011 |
| WO | WO2012082164 | 6/2012 |
| WO | WO2012152900 | 11/2012 |
| WO | WO2013041618 | 3/2013 |
| WO | WO2013104682 | 7/2013 |
| WO | WO2013169674 | 11/2013 |
| WO | WO2013173700 | 11/2013 |
| WO | WO2014070889 | 5/2014 |
| WO | WO2014088801 | 6/2014 |
| WO | WO2014090908 | 6/2014 |
| WO | WO2014095853 | 6/2014 |
| WO | WO2014143762 | 9/2014 |
| WO | WO2014198279 | 12/2014 |
| WO | WO2016148675 | 9/2016 |

OTHER PUBLICATIONS

Dai et al. "Surgical treatment of the osteoporotic spine with bone cement-injectable cannulated pedicle screw fixation: technical description and preliminary application in 43 patients," Clinics, Feb. 2015, vol. 70, No. 2, pp. 114-119.

Hong et al. "Binder-jetting 3D printing and alloy development of new biodegradable Fe—Mn—Ca/Mg alloys," Acta 3iomaterialia, Nov. 2016, vol. 45, pp. 375-386 (Abstract Only) 4 pages.

Introducing IntelliSense Drill Technology®, McGinley Orthopaedic Innovations, 1 page, [captured Feb. 29, 2016 from: http://web.archive.org/web/20160229042028/http://www.mcginleyorthopaedicin-novations.com/index.php?/pages/drill].

Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.

Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).

Lu et al. "A Novel Patient-Specific Navigational Template for Cervical Pedicle Screw Placement," Spine, Dec. 15, 2009, vol. 34, No. 26, pp. E959-E966 (Abstract Only).

Owen et al. "Rapid prototype patient-specific drill template for cervical pedicle screw placement." Computer Aided Surgery, Sep. 2007, vol. 12, No. 5, pp. 303-308 (Abstract Only).

Partial Search Report for European Patent Application No. 11804191.2, dated Jan. 20, 2015 6 pages.

Ryken et al. "Image-based drill templates for cervical pedicle screw placement Laboratory investigation," Journal of Neurosurgery, Jan. 2009, vol. 10, No. 1 (Abstract Only).

Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).

* cited by examiner

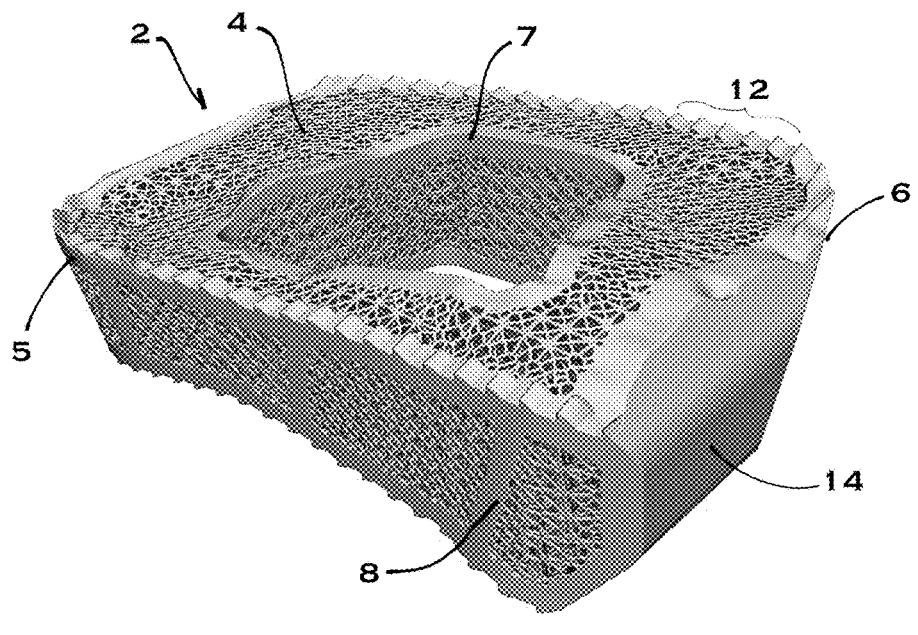
FIGURE 1A
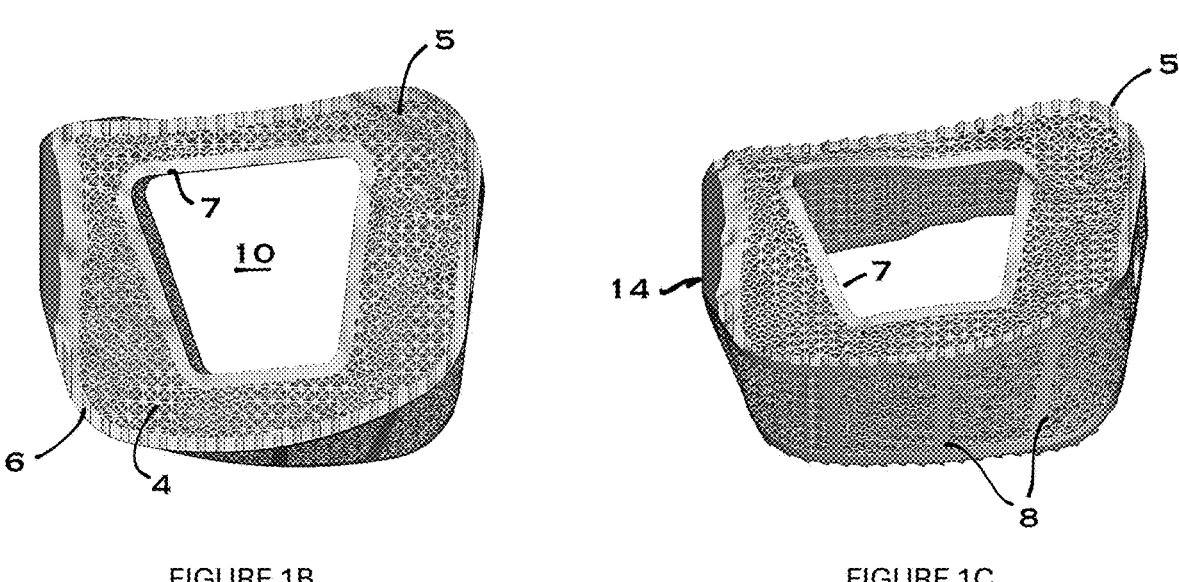
FIGURE 1B                                        FIGURE 1C

INTERBODY DEVICE INCORPORATING LATTICE STRUCTURE AND RELATED SYSTEMS AND METHODS

CROSS REFERENCE TO RELATED APPLICATIONS

This application claims the benefit of and priority to U.S. Provisional Patent Application No. 63/447,299 filed on Feb. 21, 2023, pursuant to 35 U.S.C. § 119(e). This application is also related to the following commonly-owned U.S. patent applications and patents, all of which are incorporated by reference herein for the purpose of supplementing this disclosure: U.S. patent application Ser. No. 16/831,215, filed on Mar. 26, 2020; U.S. Pat. No. 11,376,073, which issued on Jul. 5, 2022; U.S. Pat. No. 11,376,049, which issued on Jul. 5, 2022; U.S. Pat. No. 9,987,024, which issued on Jun. 5, 2018; U.S. Pat. No. 9,642,633, which issued on May 9, 2017; U.S. Pat. No. 9,198,678, which issued on Dec. 1, 2015; U.S. Pat. No. 8,870,889, which issued on Oct. 28, 2014; U.S. Pat. No. 8,758,357; which issued on Jun. 24, 2014.

FIELD OF THE INVENTION

The present disclosure generally relates to the field of medical devices, and more specifically toward patient-specific or patient-matched surgical devices, and even more specifically towards patient-matched implants incorporating a lattice or hybrid lattice structure. The present disclosure also includes related systems and methods.

BACKGROUND OF THE INVENTION

Individuals who suffer degenerative disc disease, natural spine deformations, a herniated disc, spine injuries or other spine disorders often require surgery on the affected region to relieve pain and prevent further injury. Such spinal surgeries may involve fixation of two or more adjacent vertebral bodies. For patients with varying degrees of degenerative disc disease and/or nerve compression with associated lower back pain, spinal fusion surgery or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Given the complexities of surgical procedures and the various tools, instruments, implants and other devices used in the procedures, as well as the varying anatomical differentiation between patients, it is difficult to design and/or fabricate an implant that accounts for the unique and sometimes irregular anatomical features of a particular patient. For example, the implantation of intervertebral spacers, pedicle screws, rods or other fixation devices in a patient's boney anatomy is well accepted amongst surgeons who treat various orthopedic pathologies. Although the performance of various screw constructs has become predictable, there are still multiple challenges with the placement and insertion of the orthopedic screws or other fixation devices. The challenges occur, for example, when a surgeon is unable to reference boney landmarks due to previous surgery or when the patient's anatomy is irregular in shape, or when a particular trajectory for insertion of the screws (or other fixation devices) is impeded by anatomical obstructions.

In addition, as one of ordinary skill in the art will appreciate, a patient's spinal disc(s) typically degenerate over time due in part to anatomical loading, trauma and other external stress factors. When degeneration occurs to a certain degree, neurologic and musculoskeletal issues may arise, often requiring the disc segment to be restored to its natural anatomical height. Intervertebral fusion devices or "spacers" are used to restore the disc's natural anatomical height, while also serving to facilitate the transfer of bone graft or enhanced biologics to stimulate bone growth (i.e., "fusion"). Fusion from the upper to the lower vertebral endplates is the goal of a lumbar intervertebral fusion surgery such that the restored disc height is permanent, and mobility is inhibited, in the particular segment.

Other pathologies that may be treated utilizing an intervertebral fusion device include idiopathic scoliosis, degenerative scoliosis and spondylolisthesis. These conditions result in a patient's vertebral endplates and anatomical landmarks having abnormal positions and undesirable angular relationships. Intervertebral fusion procedures may therefore be used to help correct positional and angular imbalance and effectively realign abnormal anatomy.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a customized surgical guide and/or implant based on the dynamic nature of the anatomical structures the customized guide/implant is designed to associate with. This data, while currently used by surgeons in surgery planning, is largely unused for creating a customized set of instruments or other surgical devices that are designed to complement the patient's unique anatomy.

Specific surgical procedures are often performed in the spinal and/or cephalad region of a patient. The procedures performed in these areas are often designed to stop and/or eliminate all motion, including by removal and/or destruction of some or all of the boney anatomy in the patient's boney anatomy and/or implantable fixation devices (i.e., plates or screws) for limiting movement of the boney anatomy of the particular patient. By eliminating movement, pain and degenerative disease may be reduced or avoided. A variety of implants are used in such procedures, including interbody spacers and equivalent disc-replacement implantable devices.

The use of patient-specific data sets may also assist a surgeon in selecting a desired location and/or trajectory for an implantable device so as to avoid sensitive anatomical features of a particular patient, or to secure an implantable device in a particular area for enhanced fusion between the patient's existing boney structures and the device. In other aspects, the data sets may facilitate placement of the device in an area of desired bone density. The use of patient-specific data sets also permits a surgeon to create a patient-contacting surface that is oriented to match one or more of the anatomical features represented by the data set, and thereby quickly and efficiently locate and place the patient-contacting surface(s) in the appropriate location and orientation.

Depending on surgeon and patient pathology, different surgical approaches may be used such as a Posterior Lumbar Interbody Fusion (PLIF), Transforaminal Lumbar Interbody Fusion (TLIF), Transforaminal Lumbar Interbody Fusion Oblique (TLIFO), Anterior Lumbar Interbody Fusion (ALIF), Oblique Lumbar Interbody Fusion (OLIF), Lateral Lumbar Interbody Fusion (LLIF) and Extreme Lateral Interbody Fusion (XLIF). The invention disclosed is not limited to any one of these approaches.

It would therefore be advantageous to provide patient-specific or patient-matched implants and other apparatus for use with a surgical procedure on a specific patient. It would also be advantageous to provide a customized surgical plan based on the patient's unique characteristics and/or one or more lattice or hybrid lattice implants adapted to conform to a plurality of anatomical features of a particular patient. It would also be advantageous to provide apparatus and methods to assist a surgeon in completing the surgical procedure(s) safely and efficiently.

Finally, it is also advantageous to provide a procedure and/or apparatus that otherwise significantly reduces, if not eliminates, the problems and risks noted above. Other advantages over the prior art will become known upon review of the Summary and Detailed Description of the Invention and the appended claims.

SUMMARY OF THE INVENTION

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

The present disclosure relates to a latticed surgical device, including intervertebral implants. This disclosure also relates to patient-specific or patient-matched implants having a unique lattice and/or hybrid lattice structure therein.

As one of ordinary skill in the art will understand, orthopedic and other surgeries may be performed by a number of different procedures, as opposed to conventional surgical procedures and methods, which typically require cutting of muscles, removal of bone, and retraction of other natural elements. During a MIS procedure, for example, including procedures using the apparatus of the present invention, a less destructive approach to the patient anatomy is carried out by using retractor tubes or portals, which take advantage of anatomy and current technology to limit the damage to intervening structures. Thus, it is to be expressly understood that various surgical procedures using the apparatus and systems described herein may be performed, including with sequential or simultaneous introduction of implants, spacers, rods, pins, plates, screws or other surgical devices into or between adjacent boney anatomy in order to achieve a fusion or otherwise join various portions of the vertebrae of a particular patient.

Accordingly, one aspect of the present disclosure is to provide a patient-matched implant, at least a portion of which comprises a lattice or hybrid-lattice structure, such as the implants depicted in the appended drawing figures. The implant(s) may have one or more contours or surfaces that are derived from and are complementary to a patient's unique morphology.

In another aspect, one or more systems and/or methods is disclosed for achieving a successful fusion by providing an implant comprising a combination of lattice types ranging from organic lattice to periodic lattice and a hybrid combination of periodic and organic lattice, as will be described in greater detail below. By way of example, an implant having an organic lattice structure may better facilitate boney ingrowth between the adjacent or surrounding anatomical bodies while an implant having a periodic lattice may have improved structural integrity.

According to yet another aspect, the use of patient-specific data permits the patient-matched implant to be manufactured with defined lattices and/or apertures in the body of the implant at desired locations, about predetermined contours and/or facets of the patient-matched implant, or in specific alignment with patient-specific anatomical properties (by way of example but not limitation, a patient's unique morphology, bone density or biocompatibility).

In another aspect, the apparatus described herein is not an intervertebral implant. Other examples of implantable devices contemplated herein include but are not limited to spacers, replacement joints, replacement systems, cages, etc.

According to one aspect, the apparatus described herein comprises at least a portion or section incorporating a periodic lattice or hybrid-lattice structure, which enables bony ingrowth through those portions of the structure, thereby facilitating biocompatibility and improving mechanical characteristics.

In another aspect, the lattice portions or sections may be designed to more closely resemble that of the patient's anatomy, in order to reduce discontinuities and stress risers at the interface between the patient and the apparatus. Bony ingrowth within one or more lattice portions in turn reduces subsidence or displacement of the apparatus, and may reduce the risk of migration or failure under dynamic loading situations.

In yet another aspect, lattice or hybrid lattice structures may be present in multiple portions or sections of the implant by varying degrees. For example, one particular lattice structure may be present on about 10-30 percent of the apparatus while another particular lattice structure may be present on about 50-80 percent of the apparatus.

In another aspect, the length, diameter, depth, and/or density of the lattice structure is selected according to the properties of adjacent patient bone, which may be derived from magnetic resonance imaging (MRI) data, computed tomography (CT) data, synthetic computed tomography (sCT) data, x-ray imaging data, bi-planar x-ray imaging data, bone densitometry scan data, medical imaging data, fluoroscopy data or other patient-specific data.

In another aspect, the apparatus comprises multiple lattice portions having multiple gradients or densities.

In another aspect, the gradient(s) is primarily along a single plane, axis or surface of the apparatus. In another aspect, multiple gradients are present along a single surface, axis or plane.

In yet another aspect, the gradient(s) is selected according to patient imaging data, including but not limited to a computed tomography scan, x-ray imaging, bi-planar x-ray imaging, magnetic resonance imaging, and bone densitometry scan.

In yet another aspect, the implant or other apparatus comprises an internal graft window, pocket or well, which may be configured to receive allograft, autograft or equivalent material. The apparatus may further comprise a coupling slot or groove for coupling the apparatus with a specific tool or instrument.

In embodiments, apparatus may be implanted using a surgical guide that is oriented in at least one trajectory. The surgical guide may be used with one or more patient-matched instruments for achieving, by way of example, a TLIF trajectory or approach to the patient's vertebrae.

In embodiments, patient-specific or patient-matched apparatus described herein may be used with various orientation or registration markers for identification by a robot. Certain guides may comprise an embedded chip, circuit or equivalent with presurgical planning information, which may be read by a machine and deliver specific instructions to a robotic surgical device, for example. Such patient-specific guides may be used on multiple levels of a patient's spine that are impacted by a particular surgical procedure, and thereby provide markers for registration and orientation without having to rescan the patient throughout the surgery. The robotic device may view the patient and position of the patient's unique anatomy through the identification of the markers, and thereby more rapidly align instrumentation controlled by the robotic equipment.

In embodiments, the patient-matched devices described herein may comprise a locating feature for a robot or other autonomous device to align the guide to a vertebra in space, for example. With multiple locating guides placed on a patient's vertebra, a robot can drill into the vertebra, affix an orientation tool, and/or orient vertebra relative to each other to meet pre-surgically planned spinal alignment. Pre-surgically planned spinal alignment may also be matched to one or more pre-bent rods, minimizing surgical time. In other embodiments, the robot or other autonomous device may be configured to perform an osteotomy with known locations of vertebra relative to each other.

In embodiments, the surgical devices described herein may be used with an AR system or associated simulation device. In one embodiment, the AR capabilities are provided in conjunction with a physical guide, while in other embodiments the capabilities are provided in conjunction with a "virtual" guide. In one embodiment, the surgical device is configured as a patient-specific pedicle screw placement guide is for use with a surgical instrument or implantable device. The pedicle screw placement guide is preferably adapted to guide intra-operative placement of pedicle screws that are used to anchor a pedicle screw spinal system onto target portion of a patient's anatomy. In one embodiment, the target portion of the patient's anatomy is a posterior element of the patient's spine, including lumbar, interbody and cervical portions of a patient's spine.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. Additionally, it should be understood that the drawings are not necessarily to scale.

In the drawings:

FIG. 1A shows a perspective view of an implant according to one embodiment of the present disclosure;

FIG. 1B shows a top plan view of the implant of FIG. 1;

FIG. 1C shows a rear perspective view of the implant of FIG. 1;

Figure 1D:
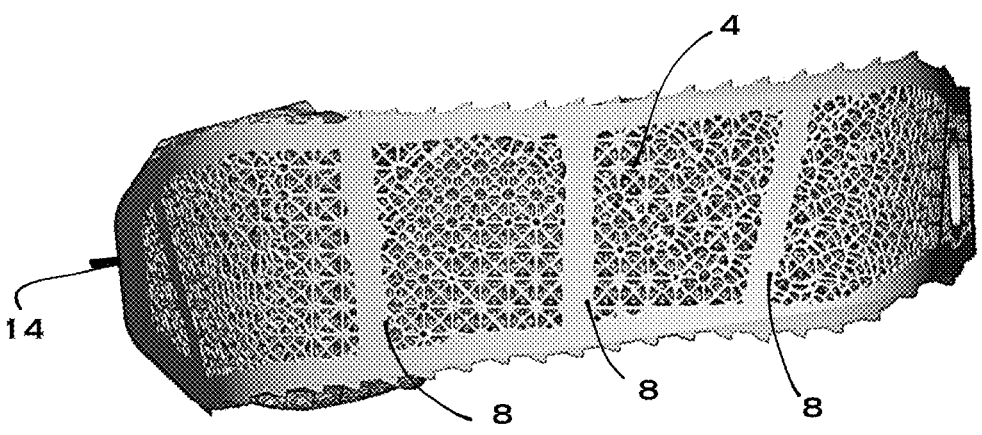
FIG. 1D shows a rear elevation view of the implant of FIG. 1.

Similar components and/or features may have the same reference number. Components of the same type may be distinguished by a letter following the reference number. If only the reference number is used, the description is applicable to any one of the similar components having the same reference number.

DETAILED DESCRIPTION

The present disclosure has significant benefits across a broad spectrum of endeavors. It is the Applicant's intent that this specification and the claims appended hereto be accorded a breadth in keeping with the scope and spirit of the disclosure and various embodiments disclosed, despite what might appear to be limiting language imposed by specific examples disclosed in the specifications. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Referring now to FIGS. 1-6, varying embodiments of the present disclosure are shown. As depicted in FIG. 1A, a patient-specific or patient-matched apparatus may be produced in the form of an implant 2. The implant 2 may comprise both lattice structure(s) 4 and solid structure(s) 6.

The lattice structure(s) 4 may be comprised of a specific geometric lattice, an organic lattice, a periodic lattice or a hybrid lattice as described more fully below. In embodiments, the implant 2 comprises one or more ribs 8 that provide structure reinforcement and/or divide specific portions or sections of lattice and/or hybrid lattice structures 4 of the implant 2. As depicted in FIGS. 1A-1C, the implant 2 may comprise solid structure(s) that form both an external frame 5 and internal frame 7, wherein internal frame 7 defines a boundary for the lattice structure(s) 4 and a well 10, which is described in detail below.

The lattice structure(s) 4 of the implant 2 provides mechanical performance benefits and improved cleanability/sterility. In preferred embodiments, the frame and/or lattice portions of implant 2 may be designed to more closely resemble that of the patient's anatomy, in order to reduce discontinuities and stress risers between the patient and the implant 2. The lattice structure(s) 4 of the implant 2 facilitate bony ingrowth within those portions of the implant 2, which in turn reduces subsidence or displacement of the implant 2 over time. In addition, an organically propagated structure (i.e., a lattice or hybrid lattice structure) conforms more easily to complex geometries often found in a patient's spine, while facilitating fusion between adjacent vertebrae. In preferred embodiments, implant 2 comprises a lattice of organic, hybrid, and periodic lattice form. A hybrid lattice structure may comprise both periodically propagated and organically propagated structures, wherein the periodically propagated lattice portions incorporated into bulk regions of the implant 2. The implant 2 may further comprise an organically propagated lattice to conform more complex geometries.

In yet another preferred embodiment, the geometric lattice portion of the implant 2, is positioned within the core structure of the implant itself and represents a periodic repeating lattice. The surface lattice is positioned on the exterior surface of the implant and reflects a, organic, hybrid, or periodic lattice structure which varies based on the shape of the implant itself. For example, if the implant is configured to fit specifically against patient anatomy, the surface lattice will take on an organic shape. If the surface lattice takes on a geometric shape, like in the case of a graft window, the lattice may be periodic. The transition between the surface lattice and the core lattice represents a transitional lattice structure that reflects a gradual transition from one lattice to another and reflects properties of each of the surface and core lattice.

Additional views of the implant 2 are illustrated in FIGS. 1B-1E. The implant 2 preferably comprises a series of ridges 12 that facilitate stability to the seating and placement of the patient contacting surfaces of the implant 2 to the patient anatomy. Thus, ridges 12 may be present on some or substantially all of the patient-contacting surfaces, which in turn serve to contact and (according to the patient's bone density) partially penetrate the patient's anatomy to secure the device in place. In one embodiment, the ridges 12 may be made of the same material and may be permanently attached to the patient contacting surfaces of implant 2. In another embodiment, the ridges 12 may be made of a different material, such as the ones described herein, and may further be selectively inserted onto one or more of the patient-contacting surfaces as desired.

Figure 1E:
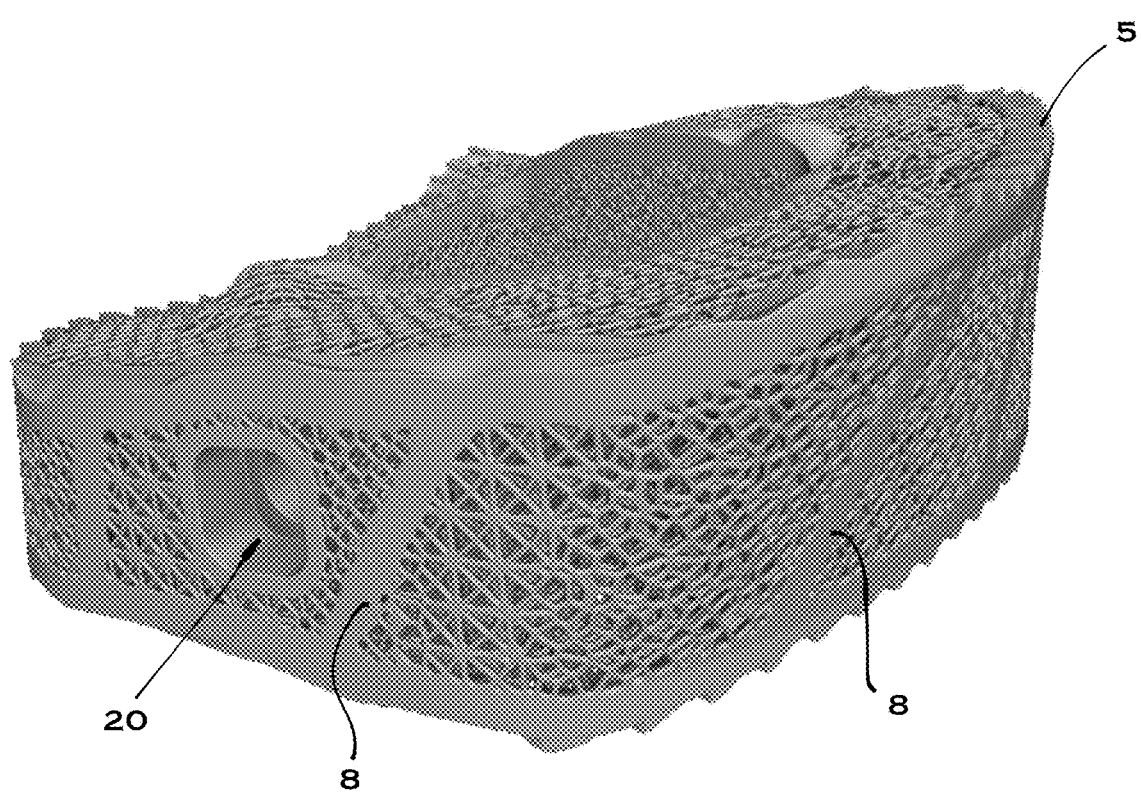
FIG. 1E shows a side perspective view of the implant of FIG. 1.

The implant 2 may have one side having a greater depth than another side, as shown in FIGS. 1D-1E. This may be incorporated into the patient-matched aspects of the implant 2 to facilitate lordosis and/or provide a desired angular relationship between the adjacent vertebral bodies. The implant 2 may further comprise a bulleted leading edge or nose 14 preferably comprising a non-latticed, solid section of the implant 2 configured for self-distraction and insertion of the implant 2. The nose 14 is also preferably devoid of ridges 12 for a smoother insertion during the procedure.

As shown in FIGS. 1A-1C, the implant 2 preferably comprises an internal pocket, well, or graft window 10, which may be configured to receive allograft, autograft or equivalent material (not shown in FIGS. 1A-1C) prior to or during insertion of the implant 2. In preferred embodiments, the implant 2 has one or more surfaces designed to mate or match with a patient's unique morphology, which may be derived from capturing MRI, CT, synthetic CT, or other patient data to derive one or more "patient matched" surfaces of the implant 2. Accordingly, implant 2 may comprise complementary surfaces based on a plurality of data points from the MRI, CT, synthetic CT, or other anatomical data.

Each "patient matched" apparatus described herein may be matched and oriented around an individual patient's unique anatomy. For instance, the implant 2 is preferably configured to incorporate specific and/or desired insertional trajectories (which may be verified in a pre-operative setting using 3D CAD software, such as the software disclosed in WO 2008027549, which is incorporated by reference herein in its entirety). Additional details regarding the different insertional trajectories are provided in the Summary and below.

Turning to FIG. 1D, multiple geometric arrangements of lattice structures 4 are depicted. For example, certain lattice structures 4 may comprise a 4-, 5- or 6-pointed star between connecting arms of the lattice. In other geometries, the lattice structure 4 may consist of a triangle, square, pentagon, hexagon, octagon or other polygon shape. Multiple shapes and numbers of interconnecting arms may be used in a single implant 2. Further illustration of the lattice structures 4 present in a single implant 2 is described in FIG. 6.

Referring now to FIG. 1E, the implant 2 may further comprise a slot 20 for coupling the apparatus with a specific tool or instrument. Although not shown in FIG. 1E, it is expressly contemplated that the instrument or tool may be configured for use in, by way of example but not limitation, a Posterior Lumbar Interbody Fusion (PLIF), Transforaminal Lumbar Interbody Fusion (TLIF), Transforaminal Lumbar Interbody Fusion Oblique (TLIFO), Anterior Lumbar Interbody Fusion (ALIF), Oblique Lumbar Interbody Fusion (OLIF), Lateral Lumbar Interbody Fusion (LLIF) and Extreme Lateral Interbody Fusion (XLIF). The distal end of the instrument or tool may be configured to fit securely (such as by an interference fit) in slot 20. Alternatively, the connection may be magnetic or provided as a latching connection.

Figures 2A, 2B, 3A, 3B, 4A, 4B:
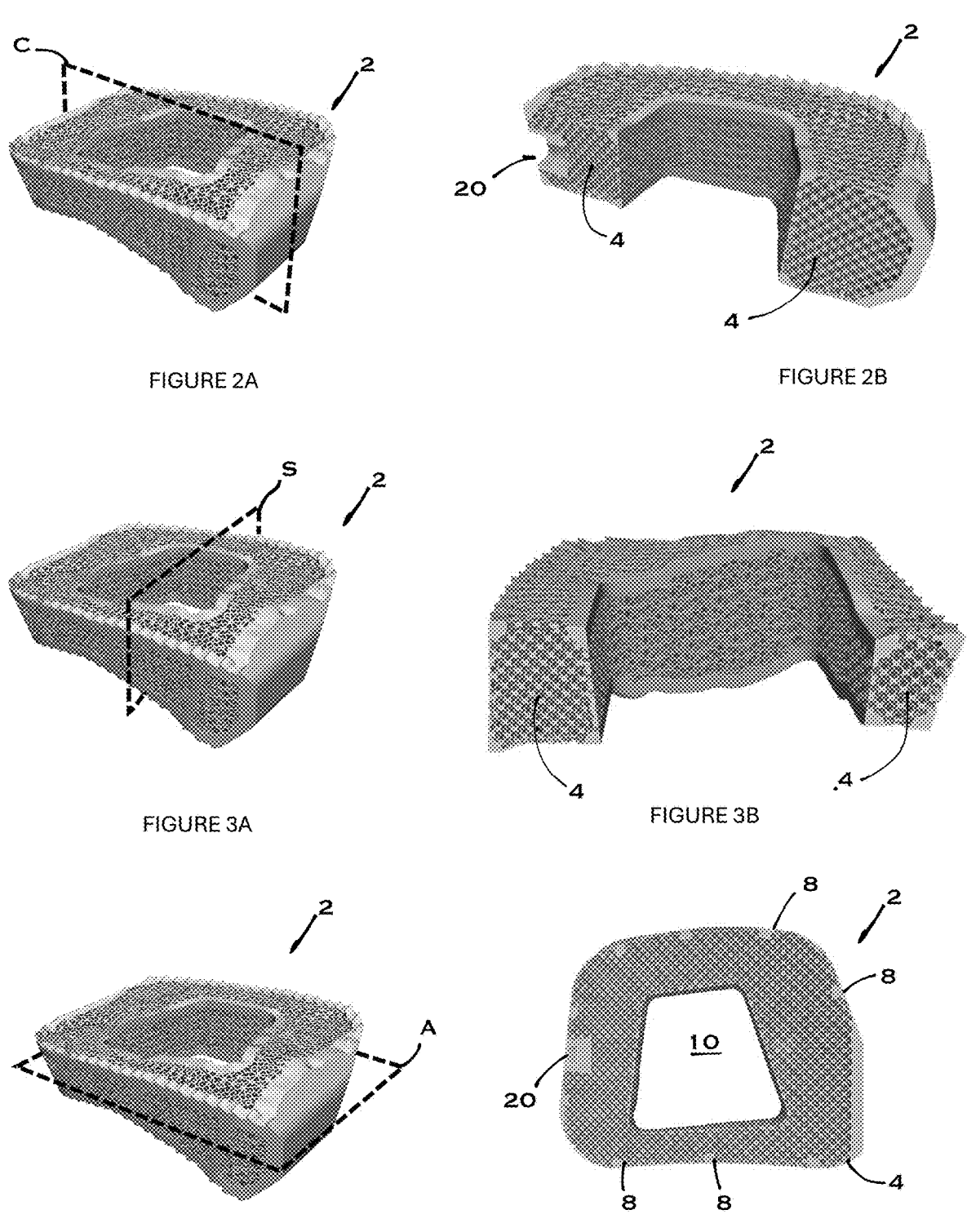
FIG. 2A shows another perspective view of the implant of FIG. 1.
FIG. 2B shows a sectional view of the implant of FIG. 2A.
FIG. 3A shows another perspective view of the implant of FIG. 1.
FIG. 3B shows a sectional view of the implant of FIG. 3A.
FIG. 4A shows another perspective view of the implant of FIG. 1.
FIG. 4B shows a sectional view of the implant of FIG. 4A.

FIG. 2A depicts the implant in an orientation to illustrate a coronal section C of the implant 2. The partial sectional view of implant 2 taken according to this coronal section C is depicted in FIG. 2B. In this section, the lattice structure 4 may be homogenous as depicted in FIG. 2B. However, in alternate embodiments the lattice structure 4 in the coronal plane may comprise multiple lattice portions, such as an organic, periodic, or hybrid lattice. The slot 20 is further shown in FIG. 2B, and in a preferred embodiment is substantially aligned with the coronal plane, in approximately the midsection of one side of the implant 2.

FIG. 3A depicts the implant in an orientation to illustrate a sagittal section S of the implant 2. The partial sectional view of implant 2 taken according to this sagittal section S is depicted in FIG. 3B. As with FIGS. 2A-2B, although the lattice structure 4 depicted is homogenous, the lattice structure 4 in the sagittal plane may also comprise multiple typed or sized lattice portions.

FIG. 4A depicts the implant in an orientation to illustrate an axial section A of the implant 2. The partial sectional view of implant 2 taken according to this axial section A is depicted in FIG. 4B. FIG. 4B depicts the preferred arrangement of ribs 8, as well as the location of slot 20 and nose 14. The lattice structure 4 in the axial plane may comprise multiple lattice portions. In certain embodiments, the lattice structures 4 may be regular and geometric, while in other embodiments they may be irregular in form. In yet other embodiments, the density of the lattice structures 4 may be homogenous throughout the implant 2, or may be heterogeneous in order to attain desired stiffness and or improve the structural interface of the solid structures 6 and lattice structures 4.

In another aspect, the lattice portions or sections may be designed to more closely resemble that of the patient's anatomy, in order to reduce discontinuities and stress risers at the interface between the patient and the apparatus. Bony ingrowth within one or more lattice portions in turn reduces subsidence or displacement of the apparatus, and may reduce the risk of migration or failure under dynamic loading situations.

In yet another aspect, lattice structures 4 may be present in multiple portions or sections of the implant by varying degrees. For example, one particular lattice structure 4 may be present on about 10-30 percent of implant 2 while another particular lattice structure 4 may be present on about 50-80 percent of the implant 2.

In another aspect, the length, diameter, depth, and/or density of the lattice structure 4 is selected according to the properties of adjacent patient bone, which may be derived from MRI, CT, bone density, medical imaging or other patient-specific data. In another aspect, the apparatus comprises multiple lattice portions having multiple gradients or densities. In another aspect, the gradient(s) is primarily along a single plane, axis or surface of the apparatus. In another aspect, multiple gradients are present along a single surface, axis or plane.

Figures 5A, 5B, 6:
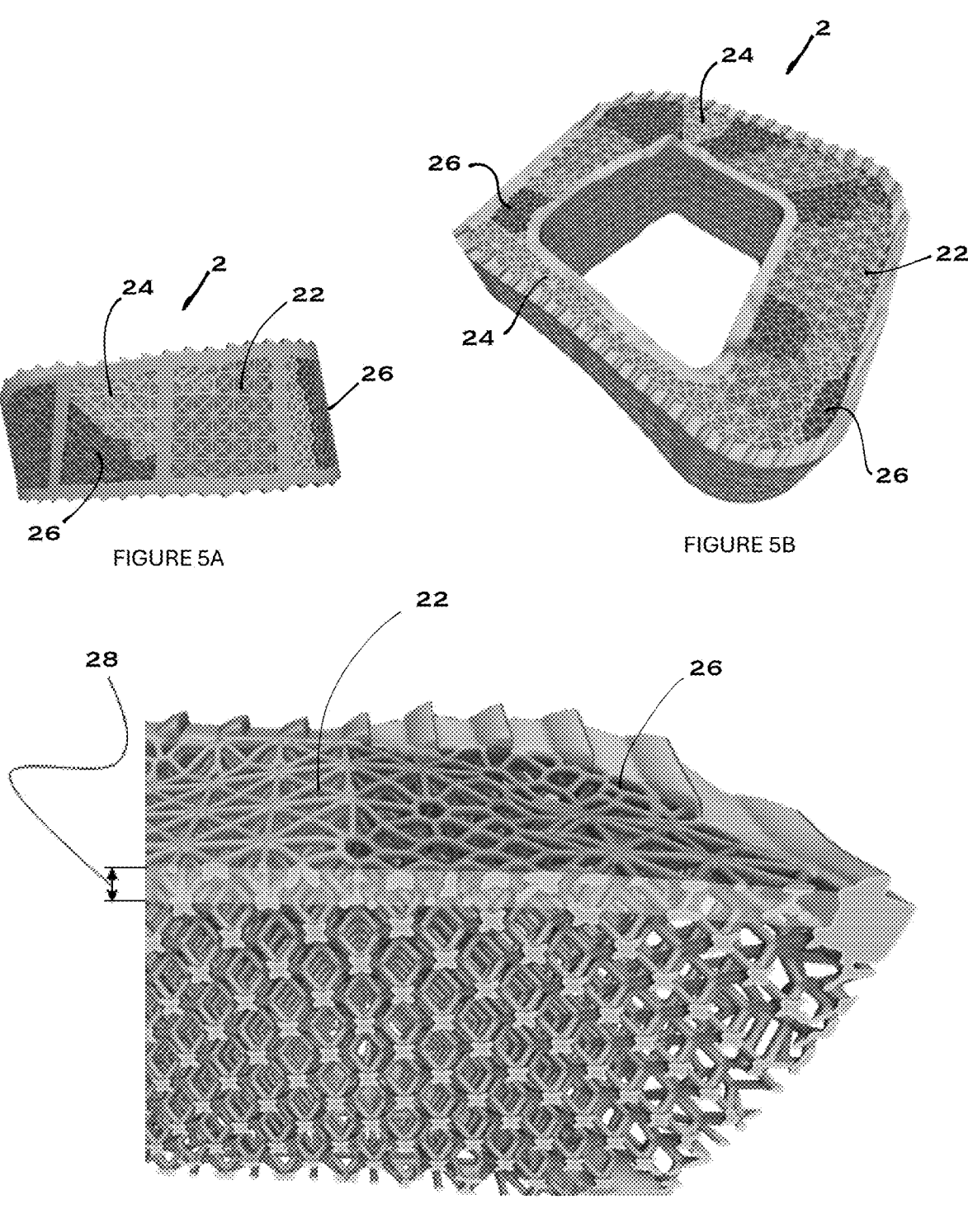
FIG. 5A shows a detailed side elevation view of the implant according to another embodiment of the present disclosure.
FIG. 5B shows a top perspective view of the implant of FIG. 5A.
FIG. 6 shows a partial sectional view of the implant according to another embodiment of the present disclosure.

Referring now to FIGS. 5A-6, additional aspects of the implant 2 are shown. Specific transitional lattice structure(s) 4 of the implant 2 may be provided in a certain, specified depth of the implant 2 (e.g., a depth of 1-5 mm). These specific lattice structure(s) 4 may not propagate from surface to surface through the implant 2. Further detail and illustration is provided below.

Referring to FIG. 5A, an implant 2 is shown having multiple surface lattice structures 4 subdivided by sections. At least a first section 22 comprises periodic lattice structures 4 present on an exterior surface of the implant 2. These regions present geometric surfaces which allow preferred propagation of a periodic (or interval based) lattice. Lattice beam lengths and subsequent pore sizes within this first section 22 of lattice structure 4 are therefore predictable and repeatable. The implant 2 further comprises at least a second section 24, which comprises a hybrid lattice structure 4 (periodic and organic) on an exterior surface of the implant 2. The lattice structures 4 present in this second section 24 are semi-geometric, which preferably allow for only partial propagation of a periodic lattice. The lattice structure 4 in this second section 24 therefore propagates only semi-predictably, as the shape of the lattice is comprised of angled segments and typically a circular shape at certain vertices. Notwithstanding, individual lattice arm length and subsequent pore size may be variable in this section 24.

The implant 2 may comprise at least a third section 26 comprising organic lattice structure 4 on an exterior surface of the implant 2. This section 26 of lattice structure 4 presents a highly complex, organic surface that does not allow for propagation of periodic lattices. The lattice forms in a "Voronoi" fashion with lattice arm lengths and subsequent pore sizes as variable. As such, the lattice structure 4 may conform to the highly complex surfaces.

Referring to FIG. 6, a partial sectional view of an implant 2 according to the embodiments shown in FIGS. 5A-5B is shown. The various surface and/or core lattice sections may be connected within a common joining section 28. The joining section 28 allows, by way of example, bulk lattice sections and surface lattice sections to connect via shared vertices. The joining section 28 thereby serves as a transitional portion of the implant that allows for a fully continuous, interconnected structure while not departing from the novelty and utility of the present invention.

In embodiments, the gradient or pattern of lattice structure 4 present in the implant 2 may be derived from, at least in part, the properties of a specific patient who receives the implant 2. For example, the particular location, arrangement and gradient of lattice structures 4 may be determined from properties of a patient's boney anatomy, including data obtained from a bone density scanner or equivalent device. Additional data may be obtained from complementary equipment, including but not limited to magnetic resonance imaging (MRI) data, computed tomography (CT) data, synthetic computed tomography (sCT) data, x-ray imaging data, bi-planar x-ray imaging data, bone densitometry scan data, medical imaging data, fluoroscopy data, sampled bone material harvested from the patient, or other anatomical data.

The gradient may result in a denser lattice structure in a first portion, and preferably comprises a gradual reduction in density approaching the exterior or patient-contacting surfaces of the implant 2. In other embodiments, the latticed portions of the implant 2 may only continue for a very short depth, while the remainder comprises solid portion(s) 6.

According to yet another aspect of the present disclosure, a method for creating an implant by use of a template is disclosed. The method includes, but is not limited to: (1) collecting data from the patient corresponding to the patient's unique anatomy; (2) creating a model of the template from the data collected, the model comprising a plurality of matching surfaces to the patient's unique anatomy; (3) providing data associated with model to fabrication machinery; (4) rapidly generating the template to comprise the plurality of matching surfaces; and (5) generating a permanent implant based on the template for use in the surgical operation.

The implant length and diameter may be pre-surgically planned to match the anatomical size of the patient's anatomy. The implant porosity and subsequent modulus may be pre-surgically planned to match the bone density of the intended patient. For example, in one embodiment, the surgical devices described above may be matched to an anatomic feature of a patient that has degenerated and needs to be restored. In another embodiment, the surgical device may be necessary to correct structural or physiological deformities present in the patient anatomy, and thereby serve to correct position or alignment of the patient anatomy. Other devices may be patient specific but do not serve a restorative or "structural" function.

The surgical devices described herein may be manufactured via additive manufacturing. In the context of spinal implants, the surgical devices may be used in all approaches (anterior, direct lateral, transforaminal, posterior, posterior lateral, anterior oblique, etc). Specific features of the surgical device can address certain surgical objectives, for example restoring lordosis, restoring disc height, restoring sagittal or coronal balance, etc. The fixation and surgical devices described herein may then be fabricated by any method. Fabrication methods may comprise the use of a rapid prototyping machine, a 3D printing machining, a stereolithography (STL) machine, selective laser sintering (SLS) machine, or a fused deposition modeling (FDM) machine, direct metal laser sintering (DMLS), electron beam melting (EBM) machine, Fused Filament Fabrication (FFF), or other additive manufacturing machine.

To add further stability to the seating and placement of the fixation devices described herein to the patient anatomy, the outer surfaces of the fixation device may further comprise other surface features, which serve to contact and at least partially penetrate or "grip" the patient anatomy to secure the fixation device in place. In one embodiment, the surface features may be made of the same material and may be permanently attached to the fixation device. In another embodiment, the surface features may be comprised of an overlay, and/or may be made of a different material, such as the ones described herein, and may further be selectively inserted onto the fixation device(s) as desired.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the apparatus described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials, rubber, latex, synthetic rubber, synthetic materials, polymers, and natural materials.

One having skill in the art will appreciate that embodiments of the present disclosure may be used in conjunction devices that employ automated or semi-automated manipulation.

The present disclosure may also be advantageous in light of recent improvements in decentralized manufacturing. For example, surgical devices may soon be capable of fabrication in a number of different and convenient settings, including but not limited to an off-site manufacturing location, an on-site manufacturing location, using equipment present in a surgeon's clinic or offices or in a public or private hospital. For example, modules may be fabricated based on a particular patient need and immediately fabricated once the need is identified, and then provided directly to the surgeon.

Additional benefits of the systems and methods described herein include improving device fixation, and/or preventing unwanted contact between devices and patient anatomy (e.g. the patient's spinal cord). The further use of methods described above, including the use of software analytics, may further aid in determining implant placement and orientation to achieve the ideal implant placement. For example, the use of various apparatus described herein to achieve desired implant placement and orientation in turn provides improved alignment of patient anatomy. This benefit in turn allows the surgeon/user to achieve optimal sagittal and/or coronal alignment, which assists in rod placement and improves correction of the patient's anatomy.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. An apparatus comprising:
   a core lattice, a surface lattice, and a transition lattice;
   wherein the core lattice is comprised of a periodic lattice structure;
   wherein the surface lattice is comprised of both periodic and organic structures, and has a different lattice shape from the core lattice;
   wherein the transition lattice comprises of both periodic and organic structures and transitions between the core lattice structure and the surface lattice structure by changing the lattice shape between the core lattice and surface lattice; and
   wherein the surface lattice defines a lattice on the surface area of the lattice boundary.

2. The apparatus of claim 1, wherein the apparatus is designed for a specific patient.

3. The apparatus of claim 1, wherein the apparatus is configured to have a patient-matched connection between an external boundary and bony anatomy at a specific implantation site.

4. The apparatus of claim 3, wherein the apparatus further comprises an external frame defining the exterior boundary of the customized apparatus.

5. The apparatus of claim 1, wherein the apparatus has an internal frame defining an internal boundary of the customized apparatus.

6. The apparatus of claim 1, wherein the apparatus has a bulleted nose.

7. The apparatus of claim 1 wherein the apparatus includes instrumentation compatibility features to interface with instrumentation.

8. The apparatus of claim 1, wherein the apparatus is comprised of at least one of a metal alloy and a polymer.

9. The apparatus of claim 1, wherein the apparatus is configured to be implanted via a posterior lumbar interbody fusion (PLIF), a transforaminal lumbar interbody fusion (TLIF), a transforaminal lumbar interbody fusion oblique (TLIFO), a lateral lumbar interbody fusion (LLIF), an oblique lumbar interbody fusion (OLIF) or an anterior lumbar interbody fusion (ALIF).

10. The apparatus of claim 4, wherein the external frame comprises one or more ridges.

11. The apparatus of claim 4, wherein the external frame comprises surface texturing.

12. The apparatus of claim 4, wherein the external frame is supported by a plurality of ribs.

13. The apparatus of claim 1, wherein the thickness of the core lattice, surface lattice, or transition lattice is non-uniform across the device.

14. The apparatus of claim 1, wherein the periodic lattice may be comprised of any periodic unit cell.

15. The apparatus of claim 1, wherein porosity of the core lattice, the surface lattice and the transition lattice structures is consistent.

16. The apparatus of claim 1, wherein porosity of the core lattice, the surface lattice and the transition lattice structures is variable.

17. The apparatus of claim 1, wherein porosity is determined based on data obtained from patient imaging.

18. A customized apparatus, comprising:
   at least one lattice structure bounded by an external frame and an internal frame;
   the internal frame defining an interior graft window of the customized apparatus;

wherein at least one of the internal frame and the external frame comprise vertically arranged ribs;

the at least one lattice structure comprising a first, periodic lattice structure, a second section comprising both periodic and organic lattice structures, and a third section comprising both periodic and organic lattice structures;

wherein the second section of the at least one lattice structure is a surface lattice;

wherein the third section of the at least one lattice structure is a transition lattice, and wherein the customized apparatus is configured to have a patient-matched connection between the customized apparatus and at least one patient-specific surface after the customized apparatus is implanted.

19. The customized apparatus of claim 18, wherein the apparatus has a bulleted nose.

* * * * *